United States Patent [19]
Kato et al.

[11] Patent Number: 5,379,347
[45] Date of Patent: Jan. 3, 1995

[54] METHOD OF INSPECTING THE SURFACE OF A WORKPIECE

[75] Inventors: Norihide Kato; Tomohide Shimizu; Kenichiro Mori, all of Sayama, Japan

[73] Assignee: Honda Giken Kogyo Kabushiki Kaisha, Tokyo, Japan

[21] Appl. No.: 988,420

[22] Filed: Dec. 9, 1992

[30] Foreign Application Priority Data

| Dec. 13, 1991 | [JP] | Japan | 3-329383 |
| Dec. 13, 1991 | [JP] | Japan | 3-329384 |
| Dec. 17, 1991 | [JP] | Japan | 3-333404 |
| Dec. 19, 1991 | [JP] | Japan | 3-337263 |

[51] Int. Cl.⁶ .................................... G06K 9/20
[52] U.S. Cl. ........................... 382/8; 356/237; 248/128; 248/92; 382/55; 382/18
[58] Field of Search ............... 382/8, 18, 55; 358/101, 358/106, 107, 183, 22; 356/237; 364/447.05, 552; 348/86, 88, 92, 125, 128

[56] References Cited

U.S. PATENT DOCUMENTS

| 4,868,404 | 9/1989 | Hajime | 356/240 |
| 4,920,572 | 4/1990 | Sugita et al. | 382/8 |
| 4,958,223 | 9/1990 | Juvinall et al. | 358/101 |
| 4,974,077 | 11/1990 | Kusaba | 382/8 |
| 4,975,972 | 12/1990 | Bose et al. | 382/8 |
| 4,980,923 | 12/1990 | Kawamoto et al. | 382/41 |
| 5,047,858 | 9/1991 | Aimonoya | 358/183 |
| 5,237,404 | 8/1993 | Tanaka et al. | 358/101 |

FOREIGN PATENT DOCUMENTS

| 0094824 | 11/1983 | European Pat. Off. . |
| 0198481 | 10/1986 | European Pat. Off. . |
| 0209252 | 1/1987 | European Pat. Off. . |
| 0263473 | 4/1988 | European Pat. Off. . |
| 0371650 | 11/1989 | European Pat. Off. . |
| 1180438 | 7/1989 | Japan . |
| 1549706 | 7/1975 | United Kingdom . |
| 2032618 | 9/1979 | United Kingdom . |
| 2102119 | 1/1983 | United Kingdom . |
| 2104651 | 3/1983 | United Kingdom . |
| 2184538 | 6/1987 | United Kingdom . |
| 2221032 | 6/1989 | United Kingdom . |
| 2239089 | 12/1989 | United Kingdom . |
| 9116619 | 10/1991 | WIPO . |

*Primary Examiner*—Leo H. Boudreau
*Assistant Examiner*—Larry J. Prikockos

[57] ABSTRACT

A method of inspecting a curved surface of a workpiece by a surface inspecting apparatus provided with a projecting device for illuminating the workpiece surface to be inspected with detection light, a detecting device for receiving and detecting the light reflected from the workpiece surface, and a condensing optical system for causing the reflected light to converge on a light-receiving surface of the detecting device. According to the method, the surface inspecting apparatus is successively displaced along the workpiece surface and the reflected light is detected by the detecting device. Further, image data obtained from the detecting device is held and binary digitized. It is determined whether or not the workpiece surface to be inspected is planar. If it is not planar, then the digitized image data is processed for dilation and erosion. Thus, when the workpiece surface is curved, faulty or defective spots can be reliably detected. If the workpiece surface is planar, the time required to process an image can be shortened.

7 Claims, 18 Drawing Sheets

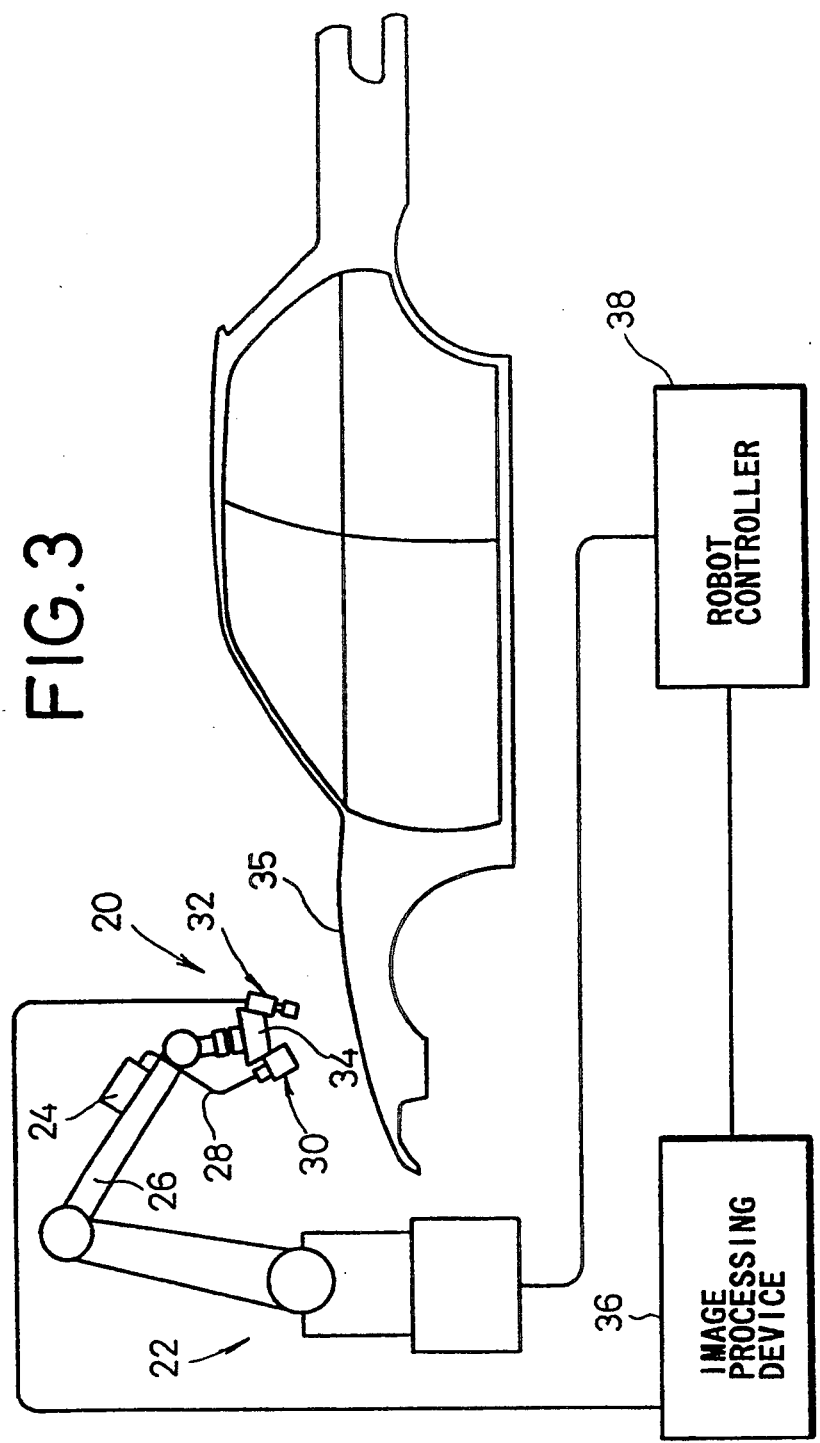

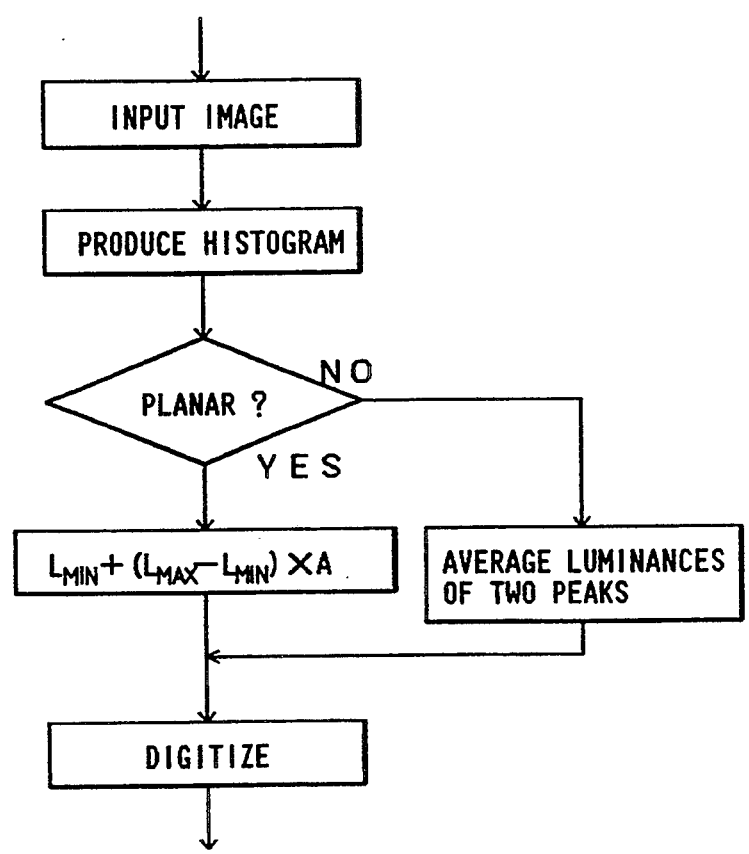

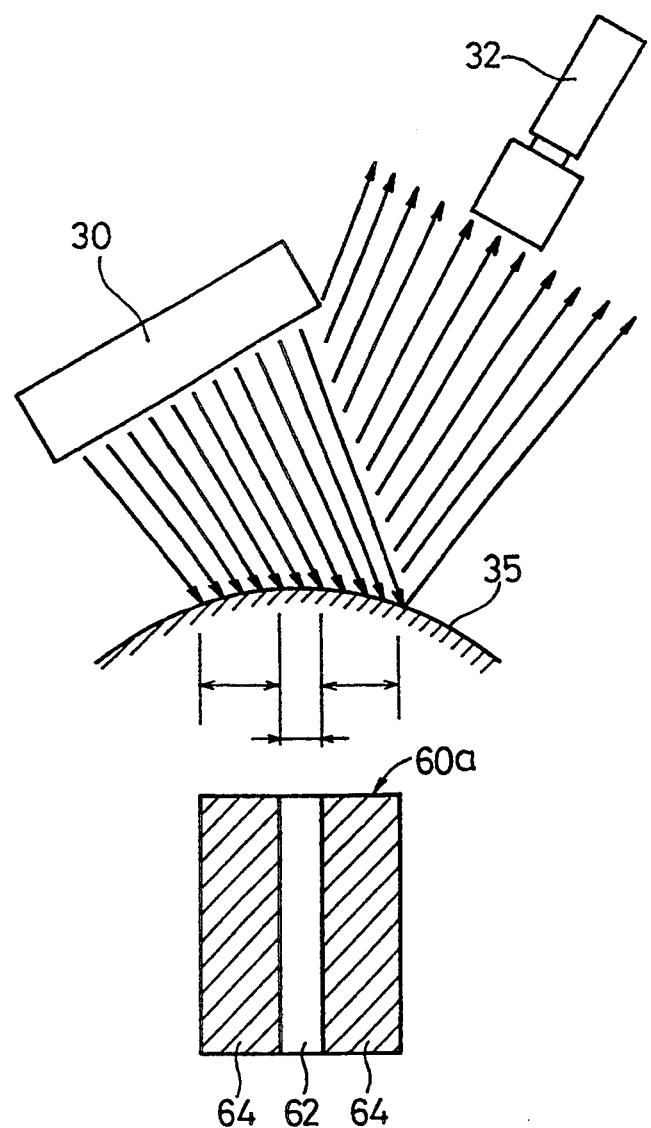
FIG.7A
FIG.7B
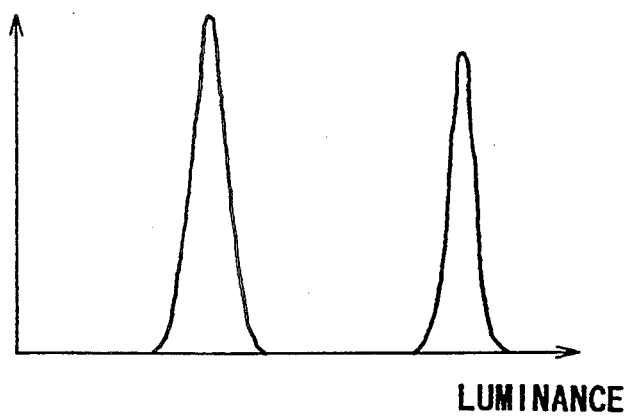
FIG.8

FIG.13

| WINDOW NO. | | WINDOW NO. | |
|---|---|---|---|
| 1 | ▨/▨ (top & bottom hatched) | 8 | ▨▢▨ (left & right hatched) |
| 2 | ▨ (bottom half hatched) | 9 | ▨ (right half hatched) |
| 3 | ▨ (top half hatched) | 10 | ▨ (left half hatched) |
| 4 | ▨ (bottom strip hatched) | 11 | ▨ (right strip hatched) |
| 5 | ▨ (top strip hatched) | 12 | ▨ (left strip hatched) |
| 6 | ▨ (top & bottom strips hatched) | 13 | ▨ (left & right strips hatched) |
| 7 | □ | 14 | □ |

FIG.16A
FIG.16B
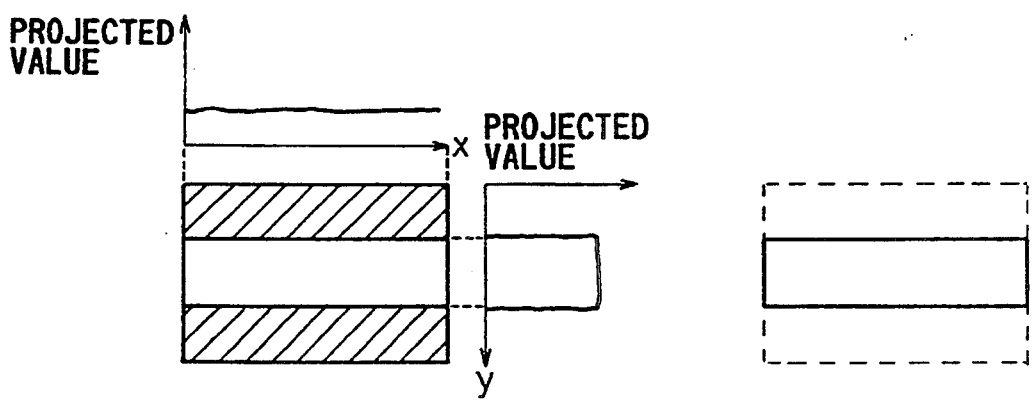
FIG.17A
FIG.17B
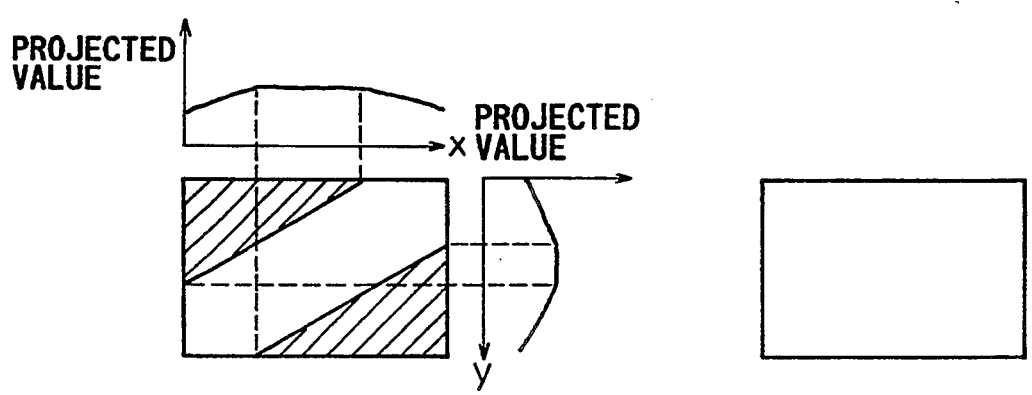

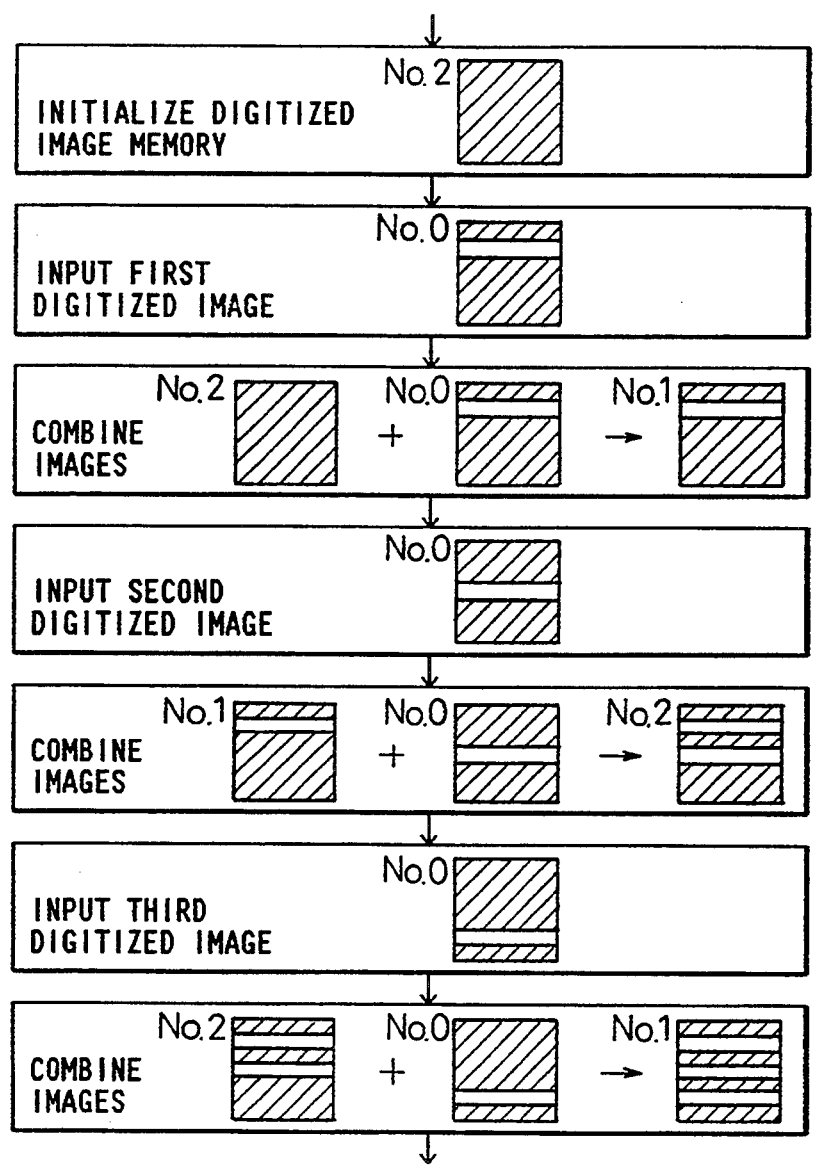

METHOD OF INSPECTING THE SURFACE OF A WORKPIECE

BACKGROUND OF THE INVENTION

1. Field of the Invention

The present invention relates to a workpiece surface inspecting method for detecting a defect in a surface such as a coated surface of a workpiece, and the degree of smoothness of the surface.

2. Description of the Background Art

A surface is inspected in the following manner. As shown in FIG. 1A, a workpiece surface 6 is irradiated via a convex lens 4 with light emitted from a projecting means 2 mounted to an arm or the like of an unillustrated robot. Then, the light is caused to converge on a detecting means 8 such as a CCD camera or the like. Further, an image 10a (see FIG. 1B) which has been detected by the detecting means 8, is subjected to image processing. Thereafter, the state of coating of the workpiece surface 6 is examined to thereby make a decision as to whether or not dust is being applied on the workpiece surface 6 and flaws exist thereon. In this case, an inspection region at which the workpiece surface 6 can be inspected at a time, can be enlarged by inspecting the workpiece surface 6 using the converged light.

In this case, the detected light satisfactorily falls on a light-receiving surface of the detecting means 8 if the workpiece surface 6 is planar. When, however, the workpiece surface 6 is curved as illustrated in FIG. 2A, the detected light is diffused from the workpiece surface 6. Therefore, a bright spot or area 12 (which is the effective inspection surface) and shadow areas 14 (which are unusable as an object to be inspected), are developed in a detected image 10b (see FIG. 2B). Further, a blurred portion is developed at the respective boundaries between the bright area 12 and each of the shadow areas 14. That is, small black spots or points (hereinafter called "isolated spots or points") tend to appear on the bright area 12 side due to the influence of the state of coating of the workpiece surface 6. Thus, when subsequent image processing is effected, the isolated points cannot be judged as being isolated points produced by the adhesion of dust, for example. Accordingly, each of the isolated points tends to be misjudged as being defects in coating. Therefore, there has been proposed a method of processing detected image data for dilation and erosion to thereby remove the isolated points from the image data.

When, however, all the detected image data are processed for dilation and erosion as described above, the time required to process the image is prolonged and the total inspection time is increased.

When the image processing is made on the entire surface of the detected image 10b, the image processing is performed even on the shadow area 14 in addition to the bright area 12, which is the effective inspection surface. Accordingly, the time required to inspect the workpiece surface is wasted and hence the entire inspection time is lengthened.

Further, such a conventional system has been disclosed in Japanese Laid-Open Patent Publication No. 1-180438, for example. According to the disclosure, a brightness/darkness-striped image projected on a surface to be inspected, is photographically recorded by an exposure means as a level signal indicative of strength and weakness of light. Then, the amount of light emitted from a light source is adjusted according to the strength of the level signal. The level signal can be detected within a predetermined range by adjusting the amount of the light emitted, irrespective of the difference in colors applied on the workpiece surface to be inspected and of any deterioration in the light source. Accordingly, any defect in the workpiece surface to be inspected can be reliably detected without a change in a predetermined defect criterion.

When the surface to be inspected is planar, defects in the surface can be satisfactorily detected once the amount of light is adjusted. The above conventional system is, however, accompanied by the problem that since the amount of light reflected by the surface to be inspected varies according to the state of exposure when the surface is curved, it is necessary to determine whether or not the level signal indicative of the strength and weakness of the light falls within a predetermined level range each time the surface to be inspected is photographically recorded and to repeatedly adjust the amount of the light accordingly. The total time required to inspect the surface is increased thereby.

SUMMARY OF THE INVENTION

It is a principal object of the present invention to provide a method of inspecting the surface of a workpiece, which is capable of reducing the time required to process an image and shortening the entire inspecting time by selectively processing detected image data for dilation and erosion.

It is another object of the present invention to provide a method of inspecting the surface of a workpiece, which can reduce the time required to process an image and shorten the entire inspecting time by performing image processing only on an effective inspection surface of a detected image.

It is a further object of the present invention to provide a method of inspecting the surface of a workpiece, which can make it unnecessary to adjust the amount of light irrespective of the shape of a surface to be inspected and suitably detect defective points from respective photographically-recorded images, thereby making it possible to shorten the entire inspection time.

According to one aspect of the present invention, for achieving the above objects, there is provided a method of inspecting a surface of a workpiece by using a surface inspecting apparatus provided with projecting means for illuminating the workpiece surface to be inspected with detection light, detecting means for receiving and detecting the light reflected from the workpiece surface, and a condensing optical system for causing the reflected light to converge on a light-receiving surface of the detecting means, including the following steps of: successively moving the surface inspecting apparatus along the workpiece surface, receiving and detecting the reflected light by the detecting means and holding image data obtained from the detecting means, binary digitizing the image data, determining whether or not the workpiece surface to be inspected is plane, and processing the digitized image data for dilation and erosion when the workpiece surface to be inspected is non-planar.

According to another aspect of the present invention, for achieving the above objects, there is provided a method of inspecting a surface of a workpiece by using a surface inspecting apparatus provided with projecting means for irradiating the workpiece surface to be inspected with detection light, detecting means for receiving and detecting the light reflected from the workpiece surface, and a condensing optical system for causing the reflected light to converge on a light-receiving surface of the detecting means, including the following steps of: selecting a preset window for extracting, based on the shape of the workpiece surface to be inspected, an effective image to be inspected from an image obtained by the detecting means, and performing image processing on an image included in an effective inspection region, the image having been extracted by using the selected window.

According to a further aspect of the present invention, for achieving the above objects, there is provided a method of inspecting a surface of a workpiece by using a surface inspecting apparatus provided with projecting means for illuminating the workpiece surface to be inspected with detection light, detecting means for receiving and detecting the light reflected from the workpiece surface, and a condensing optical system for causing the reflected light to converge on a light-receiving surface of the detecting means, including the following steps of: binary digitizing an image obtained by the detecting means, producing a histogram graphically representing a relationship between bright areas and shadow areas from the digitized image, setting a window for extracting an effective image to be inspected, based on the histogram, extracting an effective image to be inspected from the digitized image by using the set window, and performing image processing on the extracted image.

According to a still further aspect of the present invention, for achieving the above objects, there is provided a method of inspecting a surface of a workpiece by using a surface inspecting apparatus provided with projecting means for illuminating the workpiece surface to be inspected with detection light, detecting means for receiving and detecting the light reflected from the workpiece surface, and a condensing optical system for causing the reflected light to converge on a light-receiving surface of the detecting means, including the following steps: a first step for successively moving the surface inspecting apparatus along the workpiece surface, receiving and detecting the reflected light by the detecting means and bi-level digitizing a plurality of images obtained by the detecting means, a second step for extracting image data corresponding to an effective inspection surface of the workpiece irradiated with the detection light from the plurality of digitized image data and for holding the extracted image data without overlapping one another, and a third step for subjecting the held image data to given image processing.

To achieve the above objects, there is provided a method of inspecting a surface of a workpiece, further comprising a fourth step for teaching the surface inspecting apparatus in advance so as to avoid the overlapping of the plurality of image data on one another.

To achieve the above objects, there is provided a method of inspecting a surface of a workpiece, wherein the second step includes a step for setting a window used to define a region corresponding to the effective inspection surface, based on the extracted digitized image data and a step for holding image data corresponding to the effective inspection surface without overlapping one another, the image data having been extracted by the window.

According to a still further aspect of the present invention, for achieving the above objects, there is provided a method of inspecting a surface of a workpiece by using a surface inspecting apparatus provided with projecting means for illuminating the workpiece surface to be inspected with detection light, detecting means for receiving and detecting the light reflected from the workpiece surface, and a condensing optical system for causing the reflected light to converge on a light-receiving surface of the detecting means, including the following steps of: successively moving the surface inspecting apparatus along the workpiece surface, receiving and detecting the reflected light by the detecting means and holding images obtained by the detecting means as tone image data for every pixel, creating a histogram graphically representing the number of pixels corresponding to respective tone levels based on the tone image data, setting a threshold value represented in a digitized level between the maximum value of a tone level in the histogram as seen on the bright area side and the maximum value of a tone level in the histogram as seen on the shadow area side, converting the tone image data into digitized image data based on the threshold value, and subjecting the digitized image data to image processing.

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

The above and other objects, features and advantages of the present invention will become apparent from the following description and the appended claims, taken in conjunction with the accompanying drawings in which preferred embodiments of the present invention are shown by way of illustrative example only, and thus are not limitative of the present invention, and wherein:

BRIEF DESCRIPTION OF THE DRAWINGS

FIG. 3 is a schematic view illustrating a workpiece surface inspecting apparatus for executing a workpiece surface inspecting method according to one embodiment of the present invention;

FIG. 6 is a fragmentary flowchart for describing the setting of a threshold value represented in a digitized level;

FIG. 7A is a view illustrating the manner in which an image on the surface of a workpiece is photographically recorded;

FIG. 7B is a view for describing the image on the surface to be inspected, which has been photographically recorded under the condition of FIG. 7A;

FIG. 8 is a histogram graphically representing brightness based on the input image;

FIGS. 12 and 12(I)–12(IV) are views for describing images on the surface of the workpiece, which has been inspected based on the workpiece surface inspecting method shown in FIG. 9A;

FIG. 13 is a view for describing windows which have been set based on the workpiece surface inspecting method shown in FIG. 9A;

FIG. 16A is a view for describing the manner in which a histogram with respect to digitized image data is set based on the workpiece surface inspecting method shown in FIG. 9A;

FIG. 16B is a view for describing a window set based on the histogram shown in FIG. 16A;

FIG. 17A is a view for describing the manner of setting of another histogram with respect to digitized image data by the workpiece surface inspecting method depicted in FIG. 9A;

FIG. 17B is a view for describing a window set based on the histogram shown in FIG. 17A;

FIG. 20 is a fragmentary schematic view for describing the combination of images by the workpiece surface inspecting method shown in FIG. 9A;

DETAILED DESCRIPTION OF THE PREFERRED EMBODIMENTS

Figure 1:
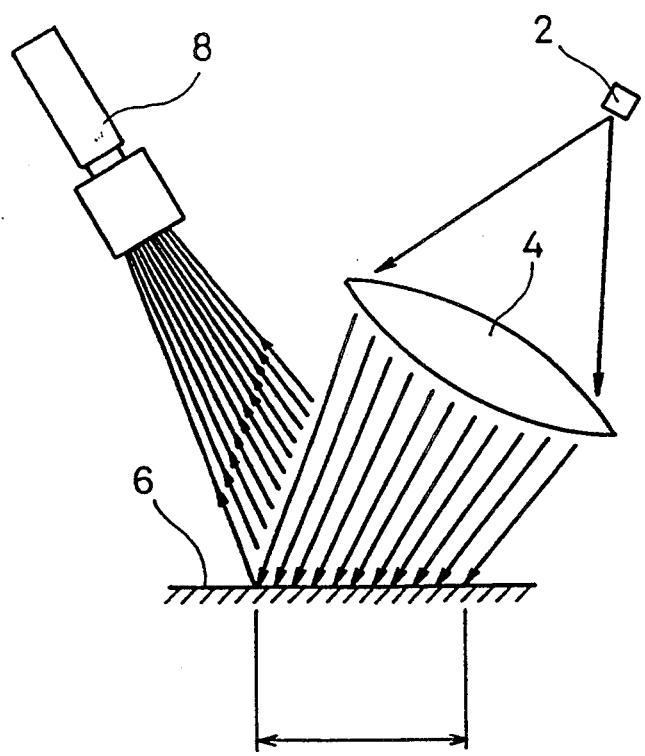
FIG. 1A is a view showing the manner in which an image of the surface of a workpiece is photographically recorded based on a conventional workpiece surface inspecting method.
FIG. 1B is a view for describing the image of the surface to be inspected, which has been photographically recorded under the condition of FIG. 1A.
Figure 1:
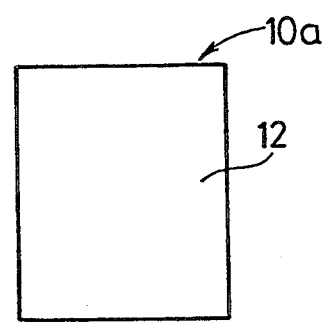
Figure 2A:
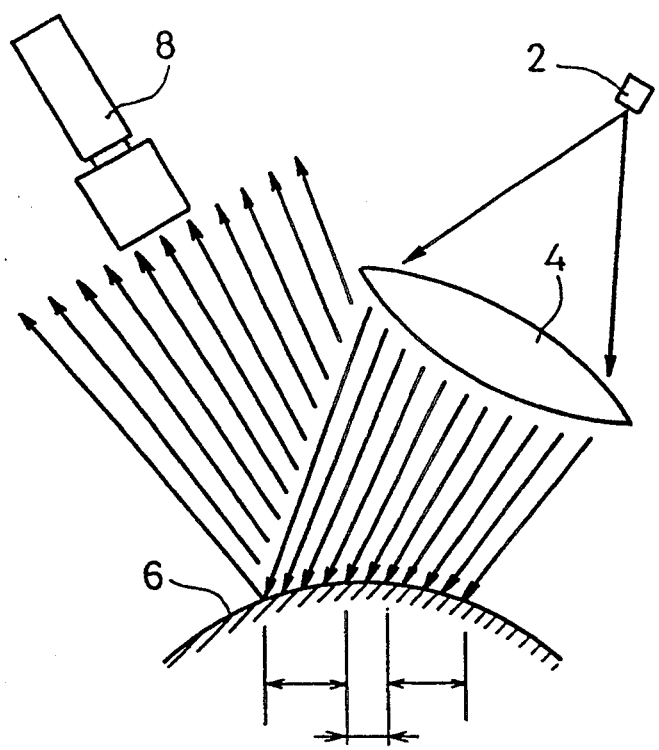
FIG. 2A is a view showing the manner in which an image of the curved surface of a workpiece is photographically recorded based on another conventional workpiece surface inspecting method.
Figure 2B:
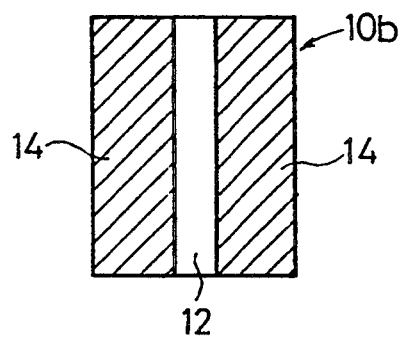
FIG. 2B is a view for describing the image on the surface to be inspected, which has been photographically recorded under the condition of FIG. 2A.

A workpiece surface inspecting method of the present invention will hereinafter be described in detail with reference to the accompanying drawings in which preferred embodiments are shown by way of illustrative example.

One embodiment of the present invention will be described based on a workpiece surface inspecting method using a workpiece surface inspecting apparatus employed in a vehicle production line.

As shown in FIG. 3, a workpiece surface inspecting apparatus 20 is mounted on a robot 22. A light source 24 is fixed to an arm 26 of the robot 22. A condensing optical system 30 is fixed to a wrist 34 and is electrically connected to the light source 24 by an optical fiber bundle 28. Optical system 30 comprises a Fresnel lens or the like, and a CCD camera 32 which serves as a detecting means. The CCD camera 32 is electrically connected to an image processing device 36 for processing an image of the surface 35 of a workpiece, for example. The image processing device 36 is electrically connected to a robot controller 38.

Figure 4:
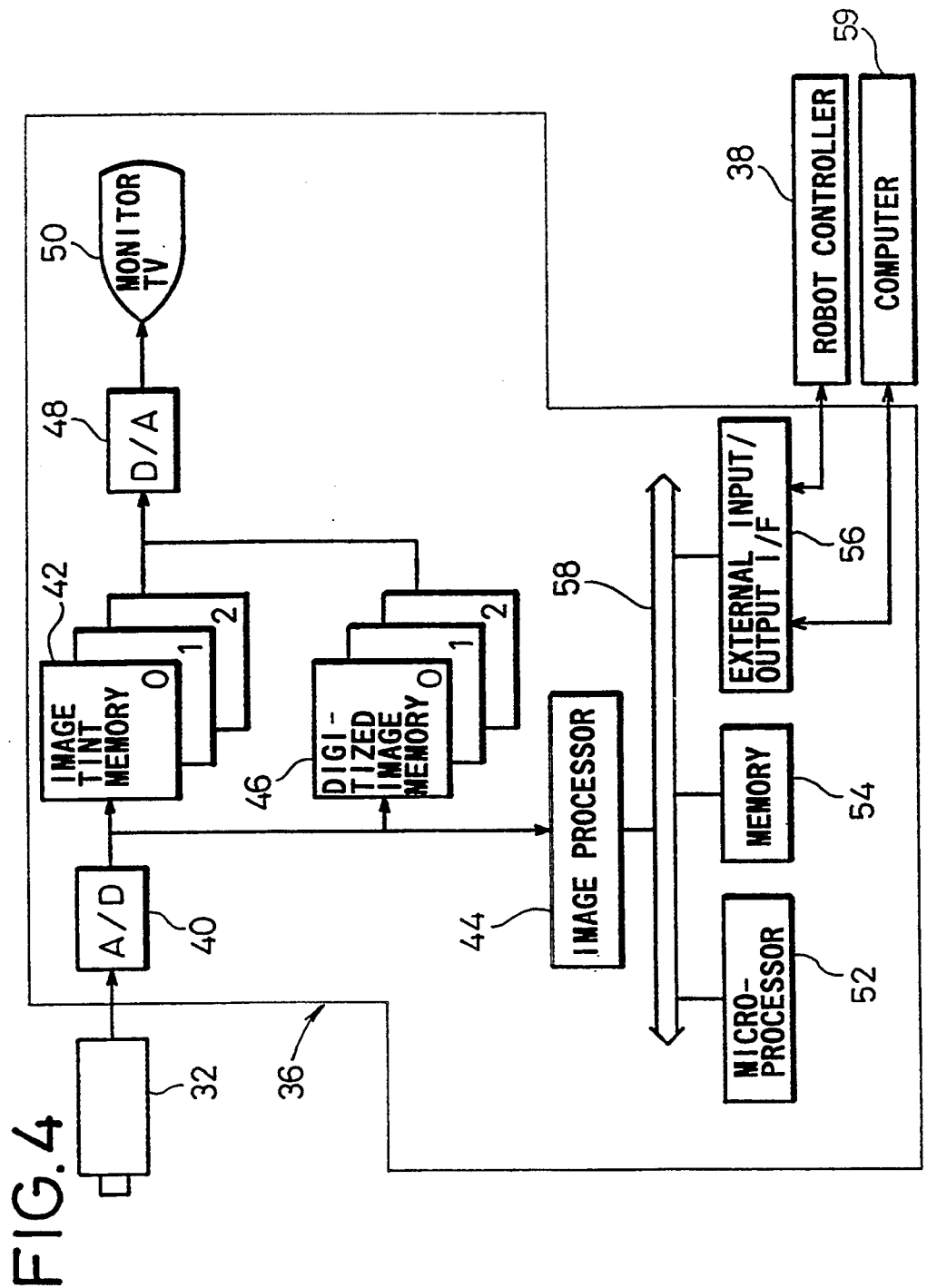
FIG. 4 is a schematic view showing an image processing device according to the present invention.

In the image processing device 36 as shown in FIG. 4, image data inputted from the CCD camera 32 is converted into a digital signal by an A/D converter 40. The converted digital signal is supplied to an image tint memory 42 as halftone or tone image data. Each of the tone image data stored in the image tint memory 42 is converted into binary digitized image data by an image processor 44. The converted image data represented in binary form is inputted to a digitized image memory 46. The tone image data stored in the image tint memory 42 and the digitized image data stored in the digitized image memory 46 are displayed on a monitor TV 50 through a D/A converter 48 as needed. The image processor 44 is electrically connected with a microprocessor 52, a memory 54, an external input/output interface I/F 56 via a bus 58. The external input/output I/F 56 is electrically connected to the robot controller 38 and an external computer 59 for controlling the result of processing.

Figure 5:
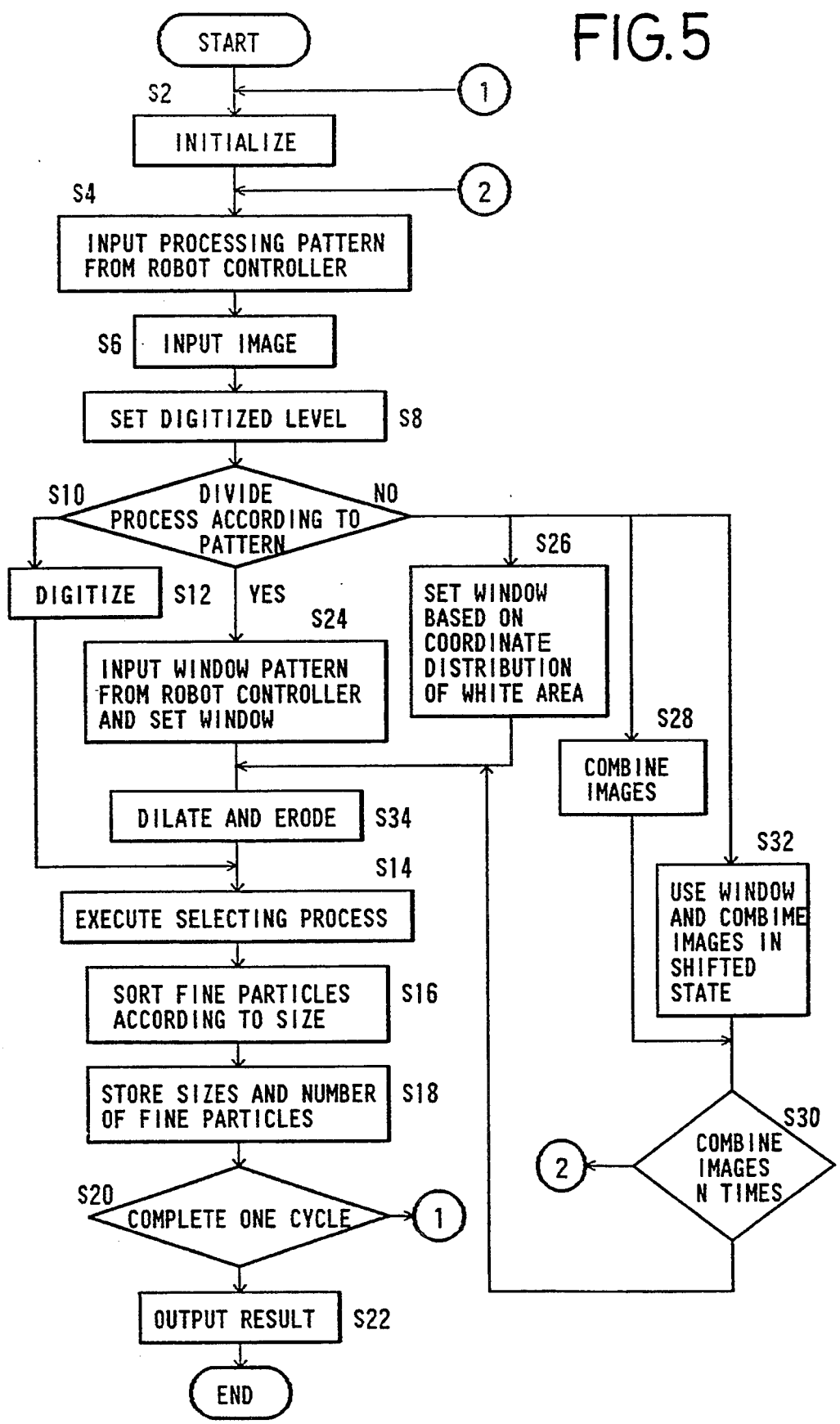
FIG. 5 is an overall flowchart for describing the workpiece surface inspecting method of the present invention.

Next, the operations of the workpiece surface inspecting apparatus 20 and the image processing device 36, which are constructed as described above, will be summarized with reference to a flowchart shown in FIG. 5.

The image processing device 36 and the robot controller 38 are first initialized (Step S2). An image processing pattern to be described later is then inputted to the image processing device 36 from the robot controller 38 (Step S4). After the above setting has been completed, the robot 22 is activated to illuminate or irradiate a predetermined range of the workpiece surface 35, a block, with inspection light emitted from the light source 24 by the optical fiber bundle 28 and the condensing optical system 30. The light reflected from the surface 35 falls on the CCD camera 32, so that image data is inputted to the image processing device 36 (Step S6).

The image data inputted to the image processing device 36 is converted into tone image data which serves as a digital signal by the A/D converter 40. The tone image data thus converted is inputted to the image tint memory 42. The image processor 44 digitizes an image so as to be expressed in a bright area and a dark or shadow area, based on a histogram graphically representing the tone image data to thereby set up a digitized level used as an identification reference (Step S8).

Predetermined image processing is effected below based on processing patterns inputted from the robot controller 38 (Step S10).

When a first processing pattern is input from the robot controller 38, i.e., when the workpiece surface 35 to be inspected is planar and the tone image data is represented in binary form, the tone image data is converted into digitized image data based on the digitized level, and the so-converted image data are stored in the digitized image memory 46 (Step S12). Then, the shadow area in the digitized image data, which exists within the bright area therein, is extracted as an isolated spot (Step S14). Based on the size of the isolated spot, it is determined and selected whether or not the isolated spot indicates dust or fine particles (Step S16). The number and sizes of fine particles which exist in one block of the processing pattern, are transferred via the external input/output I/F 56 to the computer 59, where they are stored (Step S18). The above processing is effected with respect to all of the blocks representing the workpiece surface 35 (Step 20). After the image processing on all of the blocks has been completed, the computer 59 outputs the result of inspection (Step S22).

When second and third processing patterns are input from the robot controller 38, i.e., when the workpiece surface 35 is curved and a window is set to an image taken in by the CCD camera 32, a window having a predetermined processing range is selected and a portion corresponding to a shadow area of the resultant image is deleted for the purposes of further image processing (Step S24). Alternatively, a window is determined by computation based on the distribution of the highlight of the image after the image has been digitized. Then, the shadow area or spot is deleted from the object of the image processing in a manner similar to Step S24 (Step S26).

When fourth and fifth processing patterns are input from the robot controller 38, i.e., when the workpiece surface 35 is curved and a process for combining images is selected, only the bright area is taken out from the bright area and the shadow area of a digitized image. Then, images are combined n times until image data corresponding to one frame is stored (Steps S28, S30). Alternatively, a desired window is determined by computation in a manner similar to Step S26, and images having only the bright areas, which are obtained using the determined window, are stored one frame in the digitized image memory 46 and combined into one so as not to overlap with each other (Steps S32, S30). To prevent dust or the like which exists at the boundary between the bright area and the shadow area from being misdetected, the image thus obtained is subjected to a dilation and erosion process for removing fine particles (Step S34). Thereafter, a dust detecting process, executed in Step 16, and steps subsequent to Step S16, are effected in the same manner as the first processing pattern. By performing the above processing on the image thus combined, the image processing can be collectively effected after the highlights of a plurality of images have been brought into one image, thereby enabling an improvement in image processing speed.

Now, Step S8 for executing the setting of the threshold value represented in the form of the digitized level, will be described in detail with reference to FIGS. 6 through 10.

First of all, an image on the workpiece surface 35 is inputted to the image processing device 36 from the CCD camera 32. The image is then supplied to the image tint memory 42 as tone image data. Thereafter, the image processor 44 produces a histogram graphically representing the number of pixels with respect to each brightness or luminance, based on the tone image data.

If the workpiece surface 35 is curved at this time, inspection light projected or emitted from the condensing optical system 30 is diffused by the workpiece surface 35 as illustrated in FIG. 7A. Therefore, a bright area or highlight 62 and shadow areas 64 are formed within an image 60a inputted from the CCD camera 32 as shown in FIG. 7B. Thus, the histogram includes two peaks formed so as to correspond to the bright area 62 and the shadow areas 64 as shown in FIG. 8. Now, the average value of two luminances which form the two peaks, is regarded as a threshold value represented in a digitized level. It is needless to say that the threshold value can also be set by a method other than such an averaging method if luminances between the luminances of the two peaks are used.

Figure 9A:
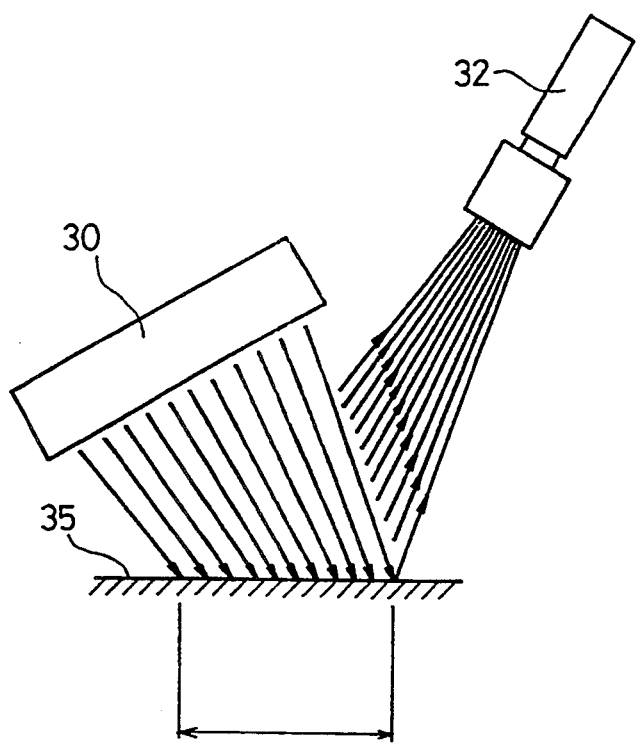
FIG. 9A is a view illustrating the manner in which an image on the surface of a workpiece is photographically recorded based on a workpiece surface inspecting method according to another embodiment of the present invention.
Figure 9B:
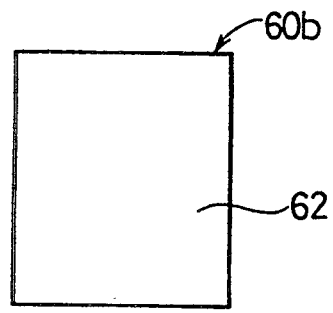
FIG. 9B is a view for describing the image on the surface to be inspected, which has been photographically recorded under the condition of FIG. 9A.
Figure 10:
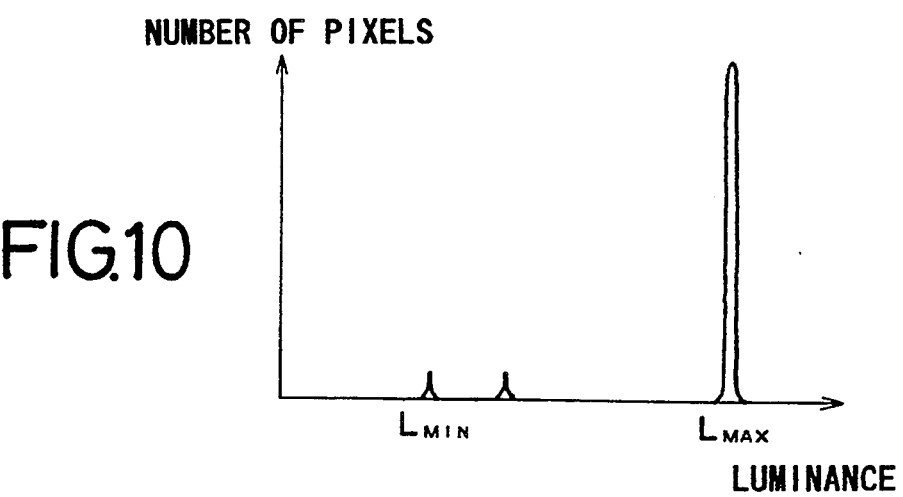
FIG. 10 is a histogram graphically representing brightness based on the input image.

When the workpiece surface 35 is planar, the inspection light projected or emitted from the condensing optical system 30 is suitably introduced into the CCD camera 32 as illustrated in FIG. 9A. Thereafter, an image 60b (see FIG. 9B) inputted from the CCD camera 32 is represented in the form of a highlight or bright area 62 alone. Accordingly, the histogram includes only a peak formed so as to correspond to the bright area 62 as shown in FIG. 10. In this case, a threshold value $\alpha$ represented in a digitized level, is determined from the following equation using the maximum luminance $L_{MAX}$, which is expressed in the histogram, corresponding to the bright area 62, and the minimum luminance $L_{MIN}$ detected owing to the presence of points where a failure in the coating on the workpiece surface 35 is developed.

$$\alpha = L_{MIN} + (L_{MAX} - L_{MIN}) \times A$$

In this equation, A represents a suitable coefficient ($0 < A < 1$). For example, A may be set equal to 0.7 (i.e., $A = 0.7$).

When, on the other hand, defective points are not developed on the workpiece surface 35 and only the peak of the bright area 62 appears, the maximum luminance $L_{MAX}$ is represented as the luminance of the peak and the minimum luminance $L_{MIN}$ is represented as 0.

In the present embodiment, when the workpiece surface 35 is curved upon setting of the digitized level, the value obtained by averaging the luminances corresponding to the respective peaks of the histogram, which are associated with the bright area 62 and the shadow areas 64 of the input image 60a, is set as the threshold value represented in the digitized level. It is therefore possible to prevent each of the shadow areas 64 from being misjudged as the bright area 62 upon digitization and to avoid the detection of the portion misjudged as a faulty or defective area upon subsequent image processing. Further, the threshold value is computed based on the maximum luminance $L_{MAX}$ and the minimum luminance $L_{MIN}$ of the input image 60b when the workpiece surface 35 is flat. It is therefore possible to set a suitable threshold value. Thus, in the present embodiment, the threshold values can be automatically changed and established with respect to the input images 60a, 60b, thereby making it possible to avoid a problem that the inspection time increases.

Figure 11:
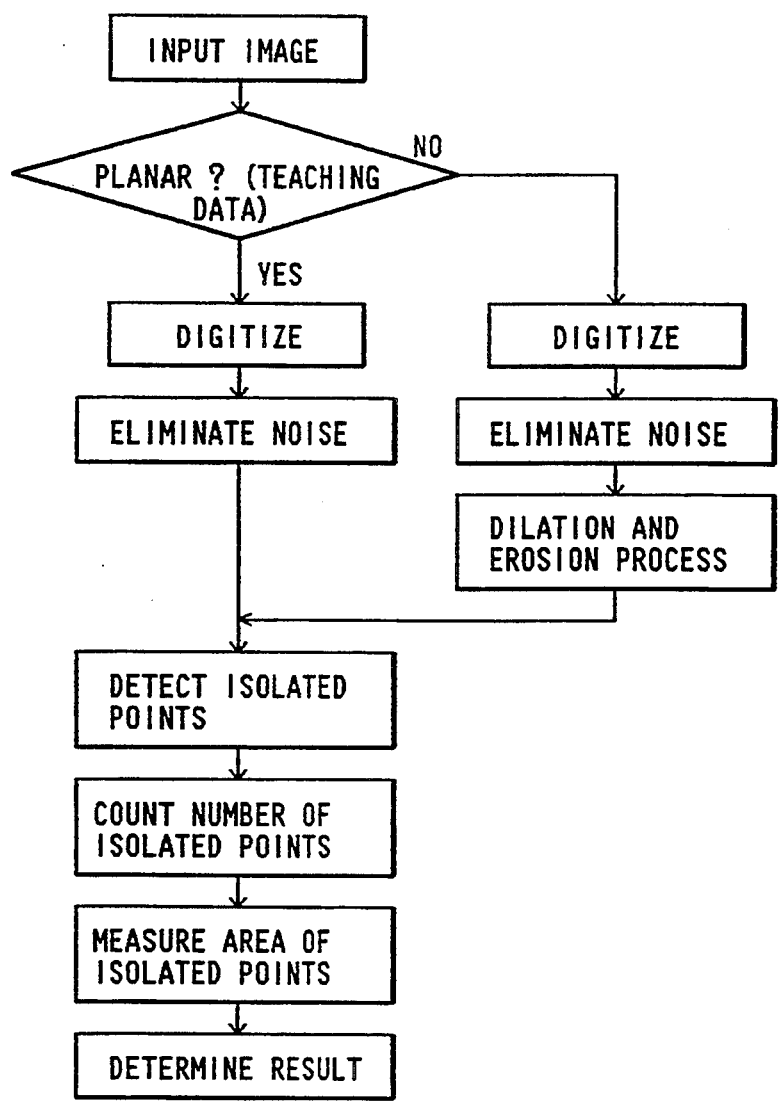
FIG. 11 is a fragmentary flowchart for describing image processing based on the workpiece surface inspecting method shown in FIG. 9A.

The summary of the workpiece surface inspecting method will next be described with reference to FIG. 11.

An image on the workpiece surface 35 is first read by the CCD camera 32. The read image is then supplied to the image tint memory 42 of the image processing device 36 as tone image data. Data about a decision which has been made as to whether the workpiece surface 35 is plane, is inputted to the image processing device 36 from the robot controller 38. This decision can be made by judging whether or not the curvature of the workpiece surface 35 to be inspected is more than or equal to a preset curvature. The curvature of the workpiece surface 35 may be stored as teaching data.

When the workpiece surface 35 is planar, the tone image data is binary digitized by the image processor 44 and the digitized image data are stored in the digitized image memory 46.

Further, noise which has entered into the digitized image data and whose level is less than or equal to a predetermined level, is removed by an electrical process.

Then, isolated spots or points (isolated black portions on an image) are detected from the image data obtained in the above-described manner. The number of the isolated points is counted and the area of each isolated point is measured. It is thereafter determined, based on the results of counting and measurement, whether or not the respective isolated points are points which are inferior in coating due to dust or the like. The result of determination is outputted to the monitor TV 50.

When the workpiece surface 35 is curved, input image data is binary digitized in the same manner as when the workpiece surface 35 is planar. Then, noise whose level is less than or equal to a given level, is removed by an electrical process. In addition to such a noise removing method, the present invention discloses a window setting method or a method of reducing portions to be processed. These methods will hereinafter be described in detail.

The window setting method (i.e., the routine executed in either Step S24 or Step S26 selected in Step S10 shown in FIG. 5) used when the workpiece surface 35 is curved, will first be described below.

The routine of Step S24 will hereinafter be described in detail with reference to FIGS. 12 through 14.

When the workpiece surface 35 is curved, every block inspected by the CCD camera 32 has different effective inspection regions. When the surface of a vehicle hood or bonnet is inspected, for example, as illustrated in FIG. 12, bright and shadow areas of read images FIG.12(I) through FIG. 12(IV) are different in shape from each other depending on spots on the bonnet to be inspected. Accordingly, a plurality of windows shown in FIG. 13 is set in advance with respect to such various images in order to delete image processing spots of the shadow areas, i.e. areas other than the effective inspection regions.

Figure 14:
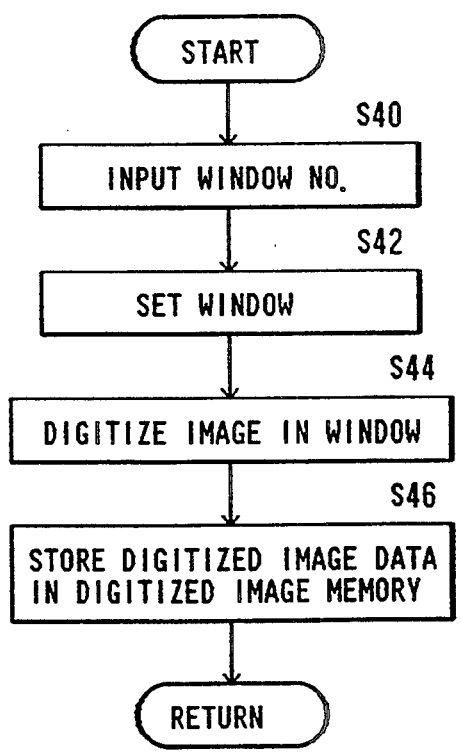
FIG. 14 is a fragmentary flowchart for describing the workpiece surface inspecting method shown in FIG. 9A.
Figure 15:
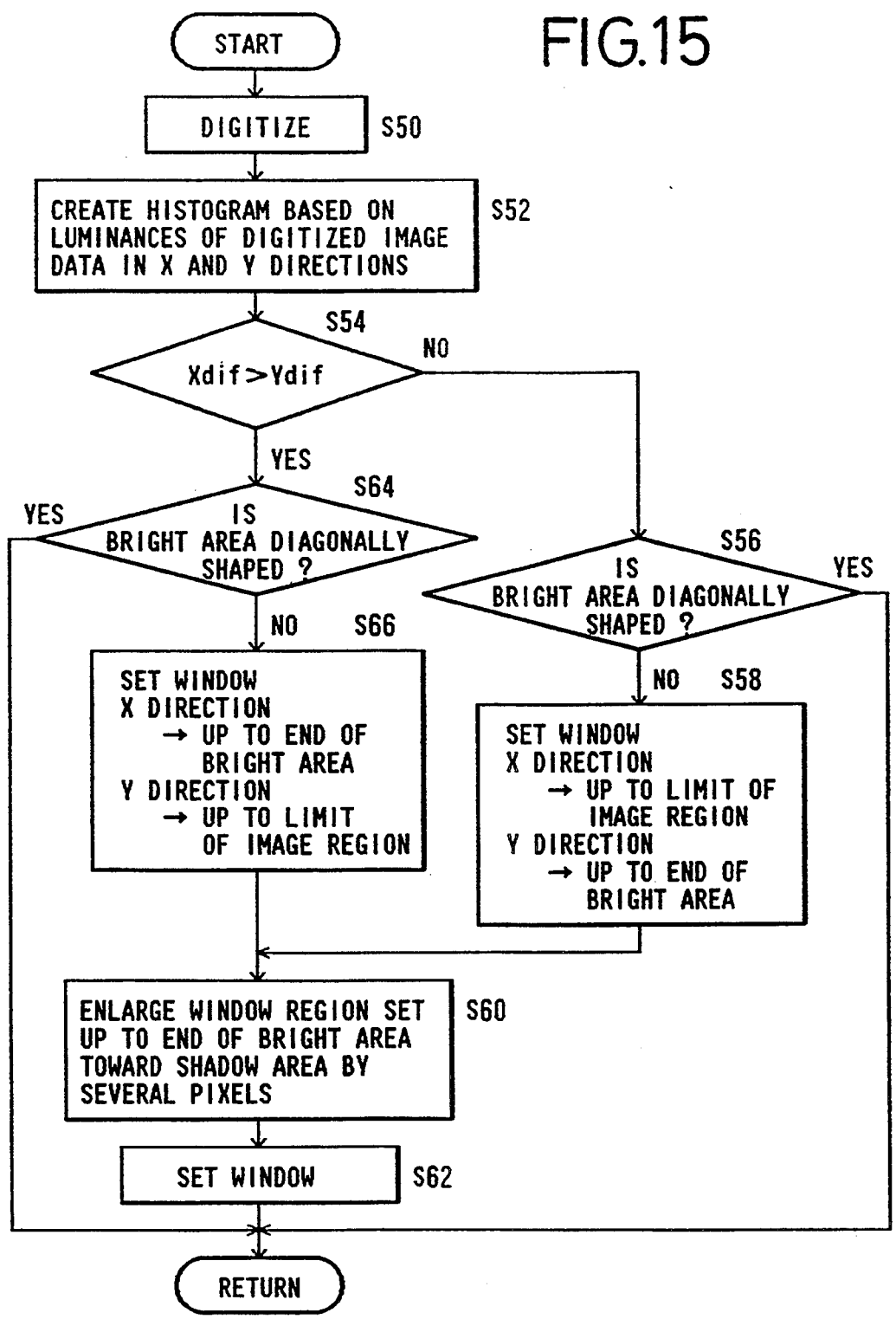
FIG. 15 is another fragmentary flowchart for describing the workpiece surface inspecting method shown in FIG. 9A.

As shown in the flowchart of FIG. 14, the robot controller 38 first inputs a predetermined window No. to the image processing device 36 in accordance with data about a point where an image on a workpiece is being read (Step S40). Then, an image inputted to the image processing device 36 from the CCD camera 32 is stored in the image tint memory 42 as tone image data. Thereafter, the image processor 44 is activated to set the window selected in Step S40 so as to correspond to the tone image data (Step S42). When the image shown in FIG. 12(I) is taken in, for example, the window No. 1 depicted in FIG. 13 is selected and set up. When, on the other hand, the image of FIG. 12(IV) is taken in, the window No. 6 is selected and set up. By setting up the windows in this way, it is unnecessary to perform the image processing in Step 34 and that subsequent to Step S34 on the majority of the shadow areas (portions indicated by oblique lines) of the taken-in images of FIGS. 12(I)–12(IV).

Figure 12:
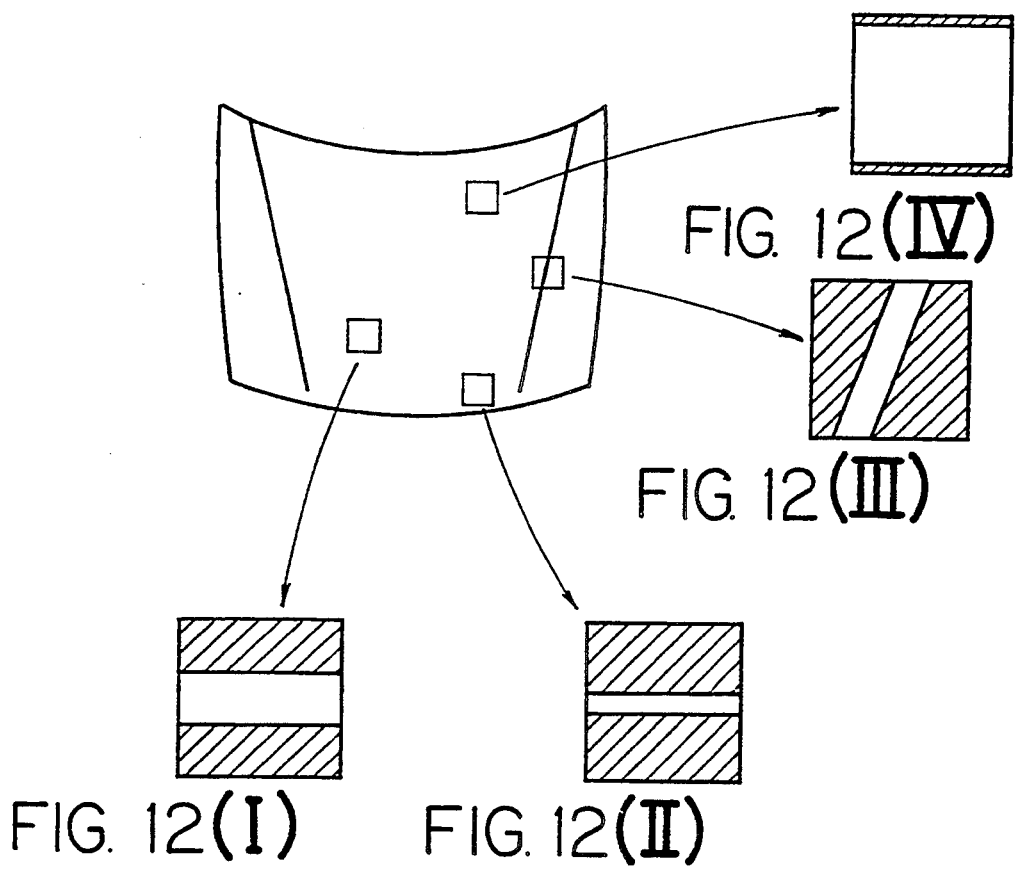

Then, image data in the windows set to the images of FIGS. 12(I)–12(IV) are binary digitized in accordance with the digitized level which has been set in Step S8 of FIG. 5 (Step 44). Further, the digitized image data are inputted to the digitized image memory 46 (Step S46). After the respective windows have been set to the images of FIGS. 12(I)–12(IV) in this way, only the images within the windows are digitized and the image processing in Step 34 and that subsequent to Step S34 of FIG. 5, is executed.

Thus, the time required to process the images can be greatly reduced because the respective windows are set to the images of FIGS. 12(I)–12(IV), and the shadow areas (i.e. areas other than the effective inspection regions) are deleted from the image processing.

Then, the routine to be executed in Step S26 will be described below with reference to FIGS. 15 through 19.

An image inputted to the image processing device 36 from the CCD camera 32 is first digitized in accordance with the digitized level which has been set in Step S8 of FIG. 5. Then, the digitized image whose bright and shadow spots or areas are represented as 1 (white) and 0 (black) respectively, is inputted to the digitized image memory 46 as image data (Step S50).

In the image processor 44, an x direction and a y direction are set as illustrated in FIG. 16A. In this condition, the number of pixels in the x direction, which correspond to bright areas of digitized image data and the number of pixels in the y direction, which correspond to bright areas of the image data, are added together so as to produce projected values, thereby creating a histogram based on the so-produced projected values (Step S52). A value $X_{dif}$ corresponding to {maximum projected value−minimum projected value} in the x direction of the histogram is compared with a value $Y_{dif}$ corresponding to {maximum projected value−minimum projected value} in the y direction thereof (Step S54). This comparison is effected to determine whether an actually-set window extends in the x or y direction. When the digitized image data shown in FIG. 16A is used, for example, $X_{dif}$ is less than $Y_{dif}$ (i.e., $X_{dif}<Y_{dif}$). Accordingly, the window to be set extends in the x direction.

Even if digitized image data are represented in diagonal form shown in FIG. 17A, there is often a situation in which $X_{dif}$ is less than $Y_{dif}$ (i.e., $X_{dif}<Y_{dif}$). At this time, the shape of a window is set as shown in FIG. 17B. As this is identical to the case where the window is not set, it is therefore necessary to bypass the process for setting the window (as described in Steps S58 through S62, later).

It is determined whether or not the highlight or bright area of the digitized image is represented in diagonal form (Step S56).

If the answer is determined to be "No" in Step S56, then a window setting region is computed. The region is set so as to extend to the limit of an image region along the x direction and to the end of the bright area along the y direction (Step S58).

Further, a window region set to the boundary between the bright area and the shadow area, is increased several pixels toward the shadow area side (Step S60). The increase in the window region is made to avoid a situation in which information about dust or the like which falls within the boundary between the bright area and the shadow area, cannot be detected.

After the window region has been set in this way, a window shown in FIG. 16B is set so as to correspond to the image (Step S62).

If, on the other hand, the answer is determined to be "Yes" in Step S56, then the entire image should be regarded as being an object for image processing. Therefore, the setting of a window is not effected.

Figure 18A:
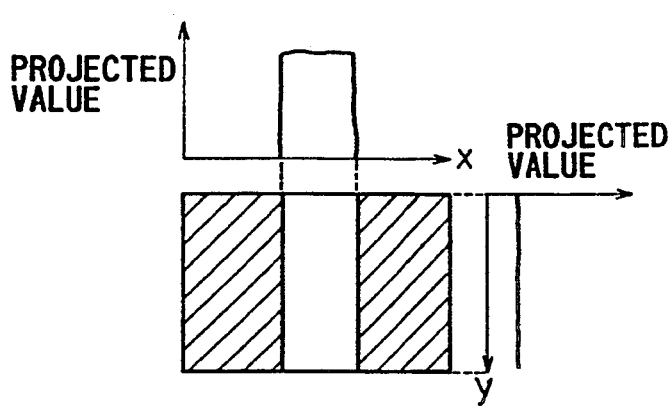
FIG. 18A is a view for describing the manner of setting of a further histogram with respect to digitized image data by the workpiece surface inspecting method shown in FIG. 9A.
Figure 18B:
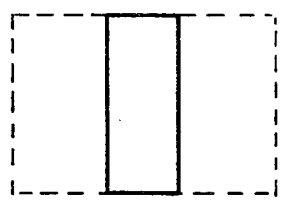
FIG. 18B is a view for describing a window set based on the histogram shown in FIG. 18A.

Similarly, if $X_{dif} > Y_{dif}$ in Step S54 as shown in FIG. 18A, then the routine similar to that executed in each of Steps S56, S58 is executed in each of Steps S64, S66. Further, the routine of each of Steps S60, S62 is executed, after which a window shown in FIG. 18B is set so as to correspond to an image.

Figure 19A:
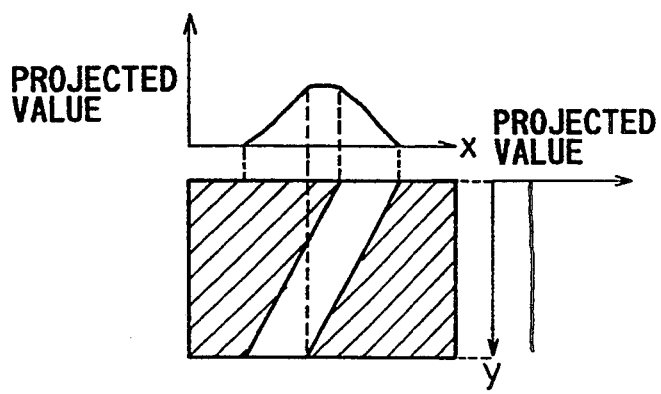
FIG. 19A is a view for describing the manner of setting of a still further histogram with respect to digitized image data by the workpiece surface inspecting method depicted in FIG. 9A.
Figure 19B:
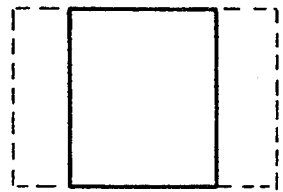
FIG. 19B is a view for describing a window set based on the histogram shown in FIG. 19A.

Note that "diagonal" herein means joining two non-adjacent corners of a rectangle, so that in FIG. 19A, the bright area is not represented in diagonal form and therefore, in accordance with the present embodiment, the image of FIG. 19A will be associated with the window of FIG. 19B, and accordingly, the shadow area to be image processed is reduced.

In the present embodiment as described above, the windows corresponding to the respective input images are set, except where the bright area is represented in diagonal form. It is therefore unnecessary to perform a dilation and erosion process to be described later on the shadow area. When the bright area is represented in diagonal form, the window setting process (Steps S58, S66 and S60) is not executed, thereby making it possible to reduce the time required to process each image.

The method (i.e., the routine executed in either Step S28 or Step S32 selected in Step S10 shown in FIG. 3) of combining the images obtained when the workpiece surface 35 is curved, will next be described in detail.

The image combining routine of Step S28 will be described below with reference to FIGS. 3 through 5 and FIG. 20.

In this case, all the storage regions of binary memories No. 0 through No. 2 which constitute the digitized image memory 46, are initially set to 0 (black).

Then, an image at a first block is inputted to the image processing device 36 from the CCD camera 32. The operation of the arm 26 of the robot 22 and the position of the CCD camera 32 are controlled, upon teaching the robot 22, by the robot controller 38, thereby positionally adjusting a bright spot or area so as to be brought to an upper portion of a frame to the CCD camera 32. The input image is first stored in the image tint memory 42 as tone image data. Thereafter, the image is bi-level digitized based on the digitized level which has been set in Step S8 shown in the flowchart of FIG. 5. The digitized image whose bright and shadow spots or areas are represented as 1 (white) and 0 (black) respectively, is stored in the binary memory No. 0 of the digitized image memory 46.

Further, the images stored in the binary memories No. 2 and No. 0 of the digitized image memory 46 are ORed or OR-operated for each pixel by the image processor 44 to produce a new composite image, which is in turn stored in the binary memory No. 1 of the digitized image memory 46.

Then, the CCD camera 32 is moved by the robot controller 38. Thereafter, an image at an adjacent second block is brought into the image processing device 36 from the CCD camera 32. In this case, the bright area of the image is positionally brought to the center of the frame of the CCD camera 32 taught by the robot controller 38 to so perform. That is, the bright area of the image is set so as not to overlap the bright area of the image at the first block. Then, the image is digitized so as to represent the bright and shadow areas thereof as 1 (white) and 0 (black) respectively. Thereafter, the digitized image is re-inputted to the binary memory No. 0.

Then, the composite image stored in the binary memory No. 1 and a new image inputted to the binary memory No. 0 are OR-operated for each pixel by the image processor 44 so as to produce a combined image. In this case, the bright areas of the images at the first and second blocks do not overlap one another by the robot controller 38 taught to so perform. Thus, as is apparent from FIG. 20 schematically illustrating the combination of the images, the bright areas of the respective images are stored as data in the binary memory No. 2 without overlapping one another.

Similarly, the robot 22 is activated to move the arm 26 to thereby enable an image at an adjacent third block to be inputted to the binary memory No. 0 from the CCD camera 32. Then, the composite image which has been stored in the binary memory No. 2, is combined with a new image inputted to the binary memory No. 0 to produce a combined image. The image thus combined is stored in the binary memory No. 1. Even in this case, the bright areas of the images of the first, second and third blocks are stored as data as shown in FIG. 20 without overlapping one another.

Thus, the images to be inspected on the curved workpiece surface, are combined together in a continuous state of the first through third blocks into one image. Further, the image thus combined is subjected to the image processing as a single image. It is therefore possible to reduce the area of unnecessary shadow area to be subjected to the image processing and to greatly improve image processing speed as compared with the case where the three images are separately subjected to the image processing.

Incidentally, while the three images are combined into one in the present embodiment, it is, however, needless to say that the number of images to be combined into one image can be changed according to the widths of the bright areas.

Figure 21:
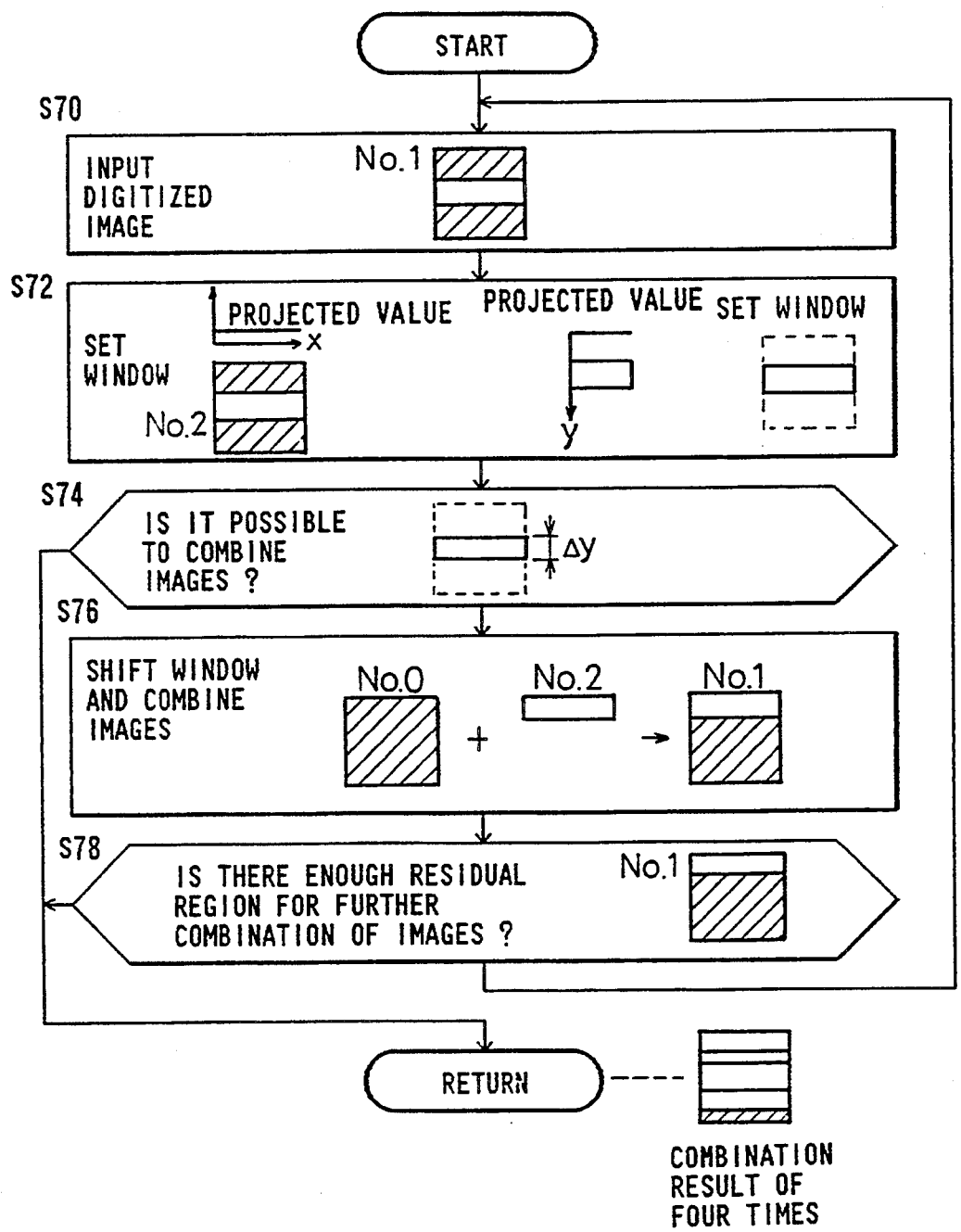
FIG. 21 is a flowchart view for describing the combination of images by the workpiece surface inspecting method shown in FIG. 9A.

Next, the image combining routine of Step S32 will be described below with reference to FIGS. 3 through 5, and a flowchart and a view for describing the combination of images, both of which are shown in FIG. 21.

First, all the storage regions of the binary memories No. 0 through No. 2 which constitute the digitized image memory 46, are initially set to 0 (black)(Step S2 in FIG. 5). Then, an image at a first block is inputted to the image processing device 36 from the CCD camera 32. The input image is first stored in the image tint memory 42 as tone image data. Thereafter, a digitized level is set in Step S8 of the flowchart shown in FIG. 5. Further, the image is binary digitized based on the digitized level. The digitized image whose bright and shadow areas are represented as 1 (white) and 0 (black)

respectively, is stored in the binary memory No. 1 (Step S70).

Then, an x direction and a y direction are set as illustrated in FIG. 21 with respect to the binary memory No. 1. In this condition, the number of pixels in the x direction, which correspond to a bright spot or area of the digitized image and the number of pixels in the y direction, which correspond to the bright area of the image, are added together so as to produce projected values, thereby creating a histogram based on the projected values. Then, a window is set based on the histogram so as to correspond to a portion equivalent to the bright area. Further, the image is divided into the bright and shadow areas by using the window again, followed by being re-inputted to the binary memory No. 2 (Step S72). It is next determined whether or not the remaining region of the binary memory No. 0 inputted with the composite image, is greater than a region delineated by a width $\Delta y$ which extends in the y direction of the window (Step S74). If the answer is determined to be "Yes" in Step S74, then the image of the binary memory No. 0 and the image of the binary memory No. 2 are OR-operated. In this case, the image of the binary memory No. 2 is combined with the image of the binary memory No. 1 in a state in which the image of the binary memory No. 2 has been shifted to the top as seen in the drawing. The image thus combined is re-inputted to the binary memory No. 1 (Step S76). Similarly, it is determined (in Step S78) whether or not there is enough remaining region in binary memory No. 1 for enabling the images to be combined again. The remaining region is compared with a predetermined region. If the answer is determined to be "Yes" in Step S78, then the image combining process to be executed in Step S70 and Steps subsequent to Step S70, is repeated. On and after a second time execution of an image combining process of Step S76, an image corresponding to a window newly produced in Step S72 is vertically (in the case of FIG. 21) or laterally juxtaposed without an overlap and without a gap with the images having been combined together in the preceding image combining process of Step S76, by adjusting the location of the newly produced window up and down in the binary memory No. 2. Thus, an image subjected to the combination four times, for example, is continuously formed based on the first to fourth image combining processes as shown below in FIG. 21.

When, on the other hand, it is determined in Step S74 that the width $\Delta y$ of the window is more than that of the remaining region of the binary memory No. 1 or when it is determined in Step S78 that the width of the residual region of the newly combined image makes it impossible to further effect an image combining process, the shifting image combining process is completed. The same effect as that obtained when the image combining process is executed in Step S28 can be brought about by effecting the above process in this way. Further, bright areas of a number of images can be combined into one by adjusting the location of the window upon combination of the images. Therefore, the memory capacity can be effectively used and the image processing speed can be improved.

Thus, when the workpiece surface is curved, the image subjected to the image processing is reduced and the dilation and erosion process is thereafter executed.

Figure 22:
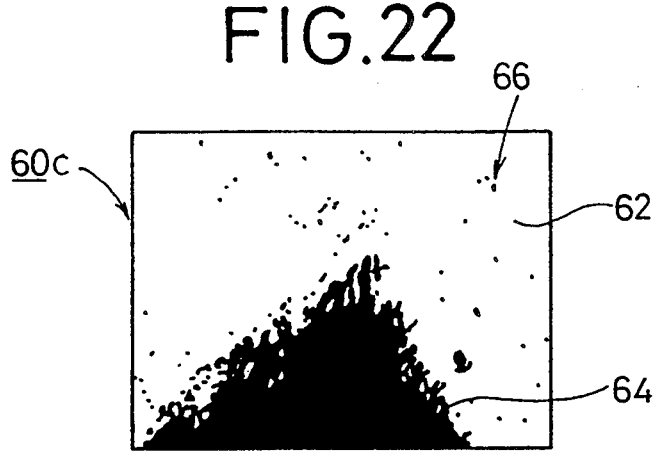
FIG. 22 is a view for describing a dilation and erosion process based on the workpiece surface inspecting method shown in FIG. 9A.

An image 60c, which has been subjected to the digitization and the noise elimination, is represented as shown in FIG. 22. That is, the state of coating of the workpiece surface has an influence on an image to be detected because the workpiece surface 35 is curved, and the boundary between a bright area 62 and a shadow area 64 is indefinite. Further, a number of isolated points or spots 66 are included in the bright area 62.

Figure 23:
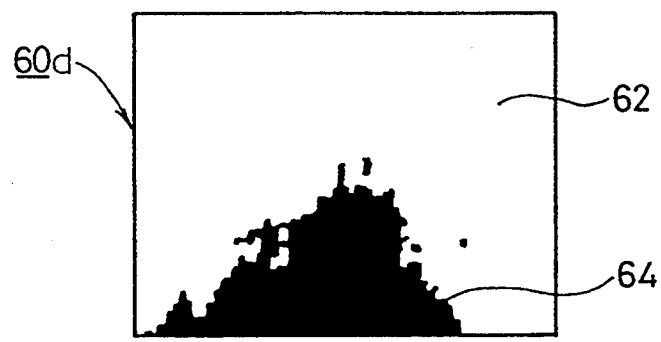
FIG. 23 is a view for describing another dilation and erosion process based on the workpiece surface inspecting method depicted in FIG. 9A.
Figure 24:
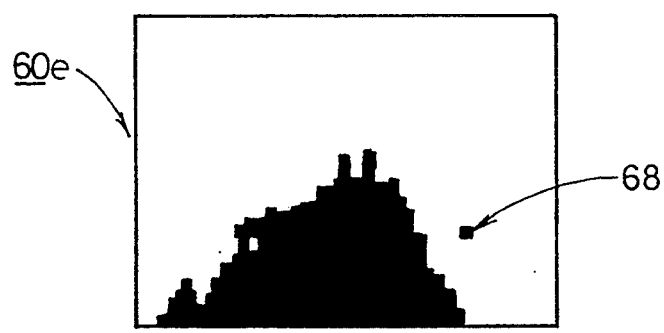
FIG. 24 is a view for describing a further dilation and erosion process based on the workpiece surface inspecting method shown in FIG. 9A.

The digitized image data shown in FIG. 22 is first processed for erosion to thereby produce an image 60d excluding unnecessary isolated points 66, each of which is not a faulty or defective point and is represented at a level below a given level, as shown in FIG. 23. Further, the image 60d is processed for dilation. As a result, the boundary between the bright area 62 and the shadow area 64 is rendered definite, thereby enabling the image 60d to be represented as an image 60e shown in FIG. 24. Further, a point or spot 68 such as dust or the like inferior in coating, which has been eroded by erosion, is dilated and hence rendered definite.

As described above, the isolated points such as the faulty point 68, etc., are detected from the image which has been processed for dilation and erosion in the same manner as when the workpiece surface 35 is planar. Then, the number of the isolated points is counted and the area of each isolated point is measured. It is also determined, based on the results of both the counting and the measurement, whether or not the respective isolated points are points such as dust, etc., which are inferior in coating. The result of determination is then outputted to the monitor TV 50.

According to the workpiece surface inspecting method of the present embodiment, as has been described above, when a workpiece surface is curved, defective points can be reliably detected by processing image data for dilation and erosion. Further, isolated points are no longer misdetected as the defective points. When, on the other hand, the workpiece surface is planar, the time required to process an image can be reduced by omitting a dilation and erosion process.

Having now fully described the invention, it will be apparent to those skilled in the art that many changes and modifications can be made without departing from the spirit or scope of the invention as set forth herein.

What is claimed is:

1. A method of inspecting a surface of a workpiece by using a surface inspecting apparatus provided with lighting means for illuminating the workpiece surface to be inspected with detection light, detecting means for receiving and detecting the light reflected from the workpiece surface, and an optical system for causing said reflected light to converge on a light-receiving surface of said detecting means, comprising the following steps of:

successively displacing said surface inspecting apparatus along the workpiece surface;

obtaining an image of the workpiece surface to be inspected by receiving and detecting said reflected light by said detecting means;

holding said image;

binary digitizing said held image;

determining whether or not the workpiece surface to be inspected is planar;

processing the digitized image for dilation and erosion only when the workpiece surface to be inspected is non-planar;

extracting isolated dark areas from said digitized image; and determining whether each of said isolated dark areas represents dust, based on the size of each of said isolated dark areas.

2. A method of inspecting a surface of a workpiece by using a surface inspecting apparatus provided with lighting means for illuminating the workpiece surface to be inspected with detection light, detecting means for receiving and detecting the light reflected from the workpiece surface, and an optical system for causing said reflected light to converge on a light-receiving surface of said detecting means, comprising the following steps of:

obtaining an image of the workpiece surface to be inspected by receiving and detecting said reflected light by said detecting means;

binary digitizing said image;

producing histograms graphically representing a configurative relationship between bright areas and dark areas of said digitized image;

setting a window in the digitized image along a boundary between said bright areas and said dark areas, based on said histograms;

expanding said window toward said dark areas to produce an expanded window;

extracting an effective image region to be inspected, surrounded by said expanded window, from the digitized image; and performing image processing on said extracted effective image region.

3. The method according to claim 2 further comprising, subsequent said step of binary digitizing, the steps of:

determining whether bright areas form a diagonal stripe crossing said digitized image; and processing said digitized image without setting a window when the bright areas form a diagonal stripe.

4. The method according to claim 2 or 3, wherein said step of performing image processing comprises the sequential steps of:

processing said extracted effective image region for dilation and erosion;

extracting isolated dark areas from the processed effective image region;

and determining whether each of the isolated dark areas represents dust, based on the size of each of the dark areas.

5. The method according to claim 4 further comprising, subsequent said step of binary digitizing, the steps of:

determining whether the workpiece surface to be inspected is planar;

extracting isolated dark areas from said digitized image without performing dilation and erosion when the workpiece surface is planar; and determining whether each of the isolated dark areas represents dust, based on the size of each of the dark areas.

6. A method of inspecting a surface of a workpiece by using a surface inspecting apparatus provided with lighting means for illuminating the workpiece surface to be inspected with detection light, detecting means for receiving and detecting the light reflected from the workpiece surface, and an optical system for causing said reflected light to converge on a light-receiving surface of said detecting means, comprising the following steps of:

teaching said surface inspecting apparatus in advance to obtain a plurality of images of the workpiece surface having bright areas located differently in respective images so that the bright areas do not overlap each other when said plurality of images are superposed on one another;

successively moving said surface inspecting apparatus along the workpiece surface in accordance with said step of teaching;

receiving and detecting said reflected light by said detecting means;

binary digitizing said plurality of images obtained by said detecting means;

extracting an image region to be inspected from each of the digitized images, corresponding to the bright area of the workpiece surface irradiated with said detection light;

holding respective extracted image regions of said plurality of images in a combined image without an overlap and without a gap between said extracted image regions;

processing said combined image for dilation and erosion;

extracting isolated dark areas from the processed combined image; and determining whether each of the isolated dark areas represents dust, based on the size of each of the dark areas.

7. A method of inspecting a surface of a workpiece by using a surface inspecting apparatus provided with lighting means for illuminating the workpiece surface to be inspected with detection light, detecting means for receiving and detecting the light reflected from the workpiece surface, and an optical system for converging said reflected light on a light-receiving surface of said detecting means, comprising the steps of:

successively moving said surface inspecting apparatus along the workpiece surface;

receiving and detecting said reflected light by said detecting means to obtain a plurality of images of the workpiece to be inspected;

binary digitizing said plurality of images;

setting a window for defining an effective inspection region in each of the digitized images corresponding to a bright area of the workpiece surface irradiated with said detection light;

extracting an image region surrounded by said window from each of the digitized images;

holding respective extracted image regions of said plurality of images in a combined image without an overlap and without a gap between said extracted image regions;

processing said combined image for dilation and erosion;

extracting isolated dark areas from the processed combined image; and determining whether each of the isolated dark areas represents dust, based on the size of each of the dark areas.

\* \* \* \* \*